United States Patent
Black et al.

(10) Patent No.: US 8,822,149 B2
(45) Date of Patent: Sep. 2, 2014

(54) PROGNOSIS PREDICTION FOR MELANOMA CANCER

(75) Inventors: Michael Alan Black, Dunedin (NZ);
Jonathan Cebon, Clifton Hill (AU);
Parry John Guilford, Dunedin (NZ);
Thomas John, East Kew (AU)

(73) Assignee: Pacific Edge Limited (NZ)

(*) Notice: Subject to any disclaimer, the term of this patent is extended or adjusted under 35 U.S.C. 154(b) by 461 days.

(21) Appl. No.: 12/592,385

(22) Filed: Nov. 23, 2009

(65) Prior Publication Data
US 2010/0136553 A1    Jun. 3, 2010

(51) Int. Cl.
*C12Q 1/68*    (2006.01)
*C12P 19/34*   (2006.01)
*C07H 21/02*   (2006.01)
*C07H 21/04*   (2006.01)

(52) U.S. Cl.
CPC .......... *C12Q 1/6886* (2013.01); *C12Q 2600/16* (2013.01); *C12Q 2600/118* (2013.01); *C12Q 2600/158* (2013.01)
USPC ........ 435/6.11; 435/91.2; 536/23.1; 536/24.3

(58) Field of Classification Search
None
See application file for complete search history.

(56) References Cited

FOREIGN PATENT DOCUMENTS

| WO | WO/2006/074330 | 7/2006 |
| WO | WO/2008/031041 | 3/2008 |
| WO | WO/2008/043018 | 4/2008 |

OTHER PUBLICATIONS

Miller, A.J. et al., Cancer res., vol. 64, pp. 509-516 (2004).*
Winnepenninckx, V et al., J. Natl. Cancer Inst., vol. 98, pp. 472-482, Suppl. 1 and 3 (2006).*
Timar, J. et al. (Clin. Exp. Metastasis, vol. 27, pp. 371-387 (2010).*
Ren, S. et al., Cancer Control, vol. 15, pp. 202-215 (2008).*
International Search Rpt, Publication Date Oct. 17, 2008, PCT/NZ2008/000118.
Written Opinion, Publication Date Oct. 17, 2008, PCT/NZ2008/000118.

* cited by examiner

*Primary Examiner* — Teresa E Strzelecka
(74) *Attorney, Agent, or Firm* — D. Benjamin Borson; Borson Law Group, PC

(57) ABSTRACT

The invention relates to prognostic markers and prognostic signatures, and compositions and methods for determining the prognosis of cancer in a patient, particularly for melanoma. Specifically, the invention relates to the use of genetic and protein markers for the prediction of the risk of progression of a cancer, such as melanoma, based on markers and signatures of markers. In various aspects, the invention provides methods, compositions, kits, and devices based on prognostic cancer markers, specifically melanoma prognostic markers, to aid in the prognosis and treatment of cancer.

1 Claim, 10 Drawing Sheets

| Probe Name | P-value | Common | Genbank | Description |
|---|---|---|---|---|
| mwghuman30K#B:3667 | 0.049 | TXNDC5 | NM_030810 | Thioredoxin domain containing 5 |
| mwghuman30K#A:06694 | 0.049 | PILRA | NM_013439 | Paired immunoglobin-like type 2 receptor alpha |
| mwghuman30K#A:06347 | 0.049 | HLA-E | NM_005516 | Major histocompatibility complex, class I, E |
| mwghuman30K#B:2443 | 0.049 | | XM_036173 | kiaa1067; kiaa1067 |
| mwghuman30K#A:09174 | 0.049 | ITPA | NM_033453 | Inosine triphosphatase (nucleoside triphosphate pyrophosphatase) |
| mwghuman30K#B:1847 | 0.0482 | DMN | NZ_145728 | Desmuslin* |
| mwghuman30K#A:07569 | 0.0429 | GTPBP2 | NM_019096 | GTP binding protein 2 |
| mwghuman30K#A:09053 | 0.0429 | MFGE8 | NM_005928 | Milk fat globule-EGF factor 8 protein |
| mwghuman30K#A:06363 | 0.0365 | IDH1 | NM_005896 | Isocitrate dehydrogenase 1 (NADP+), soluble |
| mwghuman30K#B:9466 | 0.0365 | MRPS5 | NM_031902 | Mitochondrial ribosomal protein S5 |
| mwghuman30K#A:04768 | 0.0307 | LGALS7 | NM_002307 | Lectin, galactoside-binding, soluble, 7 (galectin 7) |
| mwghuman30K#B:5919 | 0.0295 | KCNIP2 | AF347114 | Kv channel interacting protein 2 |
| mwghuman30K#A:04955 | 0.0295 | CHST4 | NM_005769 | Carbohydrate (N-acetylglucosamine 6-O) sulfotransferase 4 |
| mwghuman30K#C:4262 | 0.0295 | | AL451139.11.67295.95669.1 | ensembl genscan prediction |
| mwghuman30K#B:5235 | 0.023 | OSIL; A170; p62B | U46752 | Human phosphotyrosine independent ligand |
| mwghuman30K#A:03491 | 0.023 | NFKBIB | NM_002503 | Nuclear factor of kappa light polypeptide gene enhancer in B-cells inhibitor, beta |
| mwghuman30K#A:00049 | 0.023 | MTCH2 | NM_014342 | Mitochondrial carrier homolog 2 (C. elegans) |
| mwghuman30K#A:04349 | 0.0136 | ARFRP1 | NM_003224 | ADP-ribosylation factor related protein 1 |
| mwghuman30K#C:0720 | 0.0136 | BABI-L | AJ131063 | Birch pollen allergen specific immunoglobulin gamma chain** |
| mwghuman30K#B:4873 | 0.0136 | TUBA1B | NM_006082 | Tubulin alpha 1b*** |
| mwghuman30K#B:7713 | 0.00371 | | AJ242956_2 | partial n-myc exon 3 |
| mwghuman30K#B:0031 | 0.000756 | PLXNB2 | AB002313 | Plexin B2 |

* This marker was previously known as kiaa0353; dmn (XM_031031)
** This marker was previously known as Immunoglobulin kappa variable 1-5 (IGKC; AJ131063)
*** This marker was previously known as similar to tubulin alpha 6; loc143712 (XM_084610)

FIGURE 1

| Cell line or tissue type | Source | Weight (g) | Volume (mL) | Concentration (mg/mL) | Total (mg) | Loaded volume |
|---|---|---|---|---|---|---|
| 786 | Kidney Ca | - | 7.25 | 0.71 | 5.2 | 2.8 |
| Ovcar 3 | Ovarian Ca | - | 5 | 0.82 | 4.1 | 2.4 |
| Ovcar | Ovarian Ca | - | 4.5 | 2.21 | 10 | 0.9 |
| J82 | Bladder Ca | - | 5 | 1.11 | 5.6 | 1.8 |
| AGS | Gastric Ca | - | 4.5 | 1.2 | 5.4 | 1.7 |
| CCRF-CEM | T-cell Leukemia | - | 2.5 | 0.34 | 0.9 | 5 |
| NCI-H460 | Lung Ca | - | 7.5 | 1.2 | 9 | 1.7 |
| U251 | Brain Ca | - | 4 | 2.27 | 9.1 | 0.8 |
| COLO | Colon Ca | - | 4 | 1.55 | 6.2 | 1.3 |
| M14 | Mel | - | 8 | 0.15 | 1.2 | 5 |
| T24 | Bladder Ca | - | 7 | 1.15 | 8 | 1.7 |
| MCF7 | Breast Ca | - | 4.5 | 2.8 | 12.6 | 0.7 |
| PC3 | Prostate Ca | - | 9.5 | 1 | 9.5 | 2 |
| HL60 | AML | - | 5 | 0.58 | 2.9 | 3.4 |
| CACO6 | Colon Ca | - | 4.5 | 0.9 | 4.1 | 2.2 |
| KATO III | Gastric Ca | - | 4 | 0.58 | 2.3 | 3.5 |
| C33A | Cervical Ca | - | 4.5 | 1.41 | 6.3 | 1.4 |
| Gastric tissue | Normal Stomach | 1.5 | 2 | 0.36 | 0.7 | 5 |
| Wilms Rhabdo | Kidney/sarcoma | 9 | 4.5 | 0.3 | 1.4 | 5 |

FIGURE 4

| Common | Genbank | Description | Left Primer | Seq number | Right Primer | Seq number | Roche Probe # |
|---|---|---|---|---|---|---|---|
| TXNDC5 | NM_030810 | Thioredoxin domain containing 5 | gcacttcgtcatgtcttg | 1 | actttgcatctccatgct | 2 | 14 |
| PILRA | NM_013439 | Paired immunoglobulin-like type 2 receptor alpha | aggggaccaacaaactctccatc | 3 | tccaggtggtagtcatgctg | 4 | 64 |
| HLA-E | NM_005516 | Major histocompatibility complex, class I,E | ggaagacacatgctggag | 5 | gtgagtcacgtgtgtcttgg | 6 | 80 |
| ITPA | NM_033453 | Inosine triphosphatase (nucleoside triphosphate pyrophosphatase) | tctggagagttaaagcctgaac | 7 | aggctgacttgtcctcgaac | 8 | 17 |
| GTPBP2 | NM_019096 | GTP binding protein 2 | gtttgctcagtcaccaatg | 9 | gggaggtccagactctctcca | 10 | 47 |
| MFGE8 | NM_005928 | Milk fat globule-EGF factor 8 protein | agctacggtaacgatcagtgg | 11 | ccttgtaggatgccacaaaact | 12 | 21 |
| IDH1 | NM_005896 | Isocitrate dehydrogenase 1 (NADP+), soluble | gtgacatacctggtcataacttgaa | 13 | gtgtgcaaaatcttcaattgactt | 14 | 77 |
| MRPS5 | NM_031902 | Mitochondrial ribosomal protein S5 | ccgtgcttggtgcctgtg | 15 | gcatccatccgatcagtagc | 16 | 17 |
| KCNIP2 | AF347114 | Kv channel interacting protein 2 | aaggagagtttgtccgattcc | 17 | ttcatcgtccaagctgtc | 18 | 85 |
| CHST4 | NM_005769 | Carbohydrate (N-acetylglucosamine 6-O) sulfotransferase 4 | ggagcgagtgcttctccaag | 19 | tggaagaatagagccaagatgg | 20 | 18 |
| OSIL; A170;P62B | U46752 | Human phosphotyrosine independent ligand | ccctggaaccatccagtat | 21 | atgggtgagcaaaacatcgtc | 22 | 72 |
| NFKBIB | NM_002503 | Nuclear factor of kappa light polypeptide gene enhancer in B-cells inhibitor, beta | ggcttacgtcactgaggatgg | 23 | aggaaggttcatgctgatg | 24 | 76 |
| MTCH2 | NM_014342 | Mitochondrial carrier homolog 2 (C. elegans) | agggcattcttggattttcg | 25 | tgacgaggtaggccagtga | 26 | 5 |
| ARFRP1 | NM_003224 | ADP-ribosylation factor related protein 1 | gctcatgttctgtgggacttagga | 27 | cgttgcactccgcataatactt | 28 | 4 |
| | XM_084610 | similar to tubulin alpha 6; loc143712 | atccctagccatatgcgtga | 29 | ggcattgccaatctggac | 30 | 64 |
| | AJ242956_2 | partial n-myc exon 3 | ggctaccataggagacctcgt | 31 | caggcctagatgcagtagaacg | 32 | 18 |
| PLXNB2 | AB002313 | Plexin B2 | cagcaaacaagctgtcgtacg | 33 | cggatccccttgtagtaatcc | 34 | 39 |

FIG. 5

|  | Training set n=29 | | P value | Validation Set A n=10 | | P value |
|---|---|---|---|---|---|---|
|  | Good (n=13) | Poor (n=16) |  | Good (n=5) | Poor (n=5) |  |
| Median Age (years) | 35 (19-89) | 48.5 (28-74) | 0.2275† | 35 (24-73) | 49 (43-72) | 0.8125† |
| AJCC Stage | | | | | | |
| IIIB | 4 | 8 | 0.394‡ | 3 | 4 | 0.5647‡ |
| IIIC | 7 | 7 |  | 1 | 1 |  |
| IIIU | 1 | 1 |  | 1 | 0 |  |
| IV | 1 | 0 |  | 0 | 0 |  |
| Sex | | | | | | |
| Male | 5 | 8 | 0.4495‡ | 4 | 5 | 0.2723‡ |
| Female | 8 | 6 |  | 1 | 0 |  |
| Mean TTP (months) | 40.3 (24-72) | 4.1 (0-6) | <0.001§ | 52.2 (23-108) | 6.6 (1-15) | <0.0256§ |
| Tumor Infiltrating Lymphocytes | | | | | | |
| Brisk | 3 | 0 | 1‡ | 0 | 0 | 0.7523‡ |
| Non Brisk | 4 | 8 |  | 3 | 3 |  |
| Absent | 1 | 1 |  | 1 | 0 |  |
| Not Available | 5 | 7 |  | 1 | 2 |  |
| Adjuvant Interferon-α | 1 | 1 |  | 1 | 0 |  |

IIIU= Incomplete data at least IIIB
†Wilcoxon rank-sum test
‡Fisher's Exact test
§Cox proportional hazards

FIGURE 6

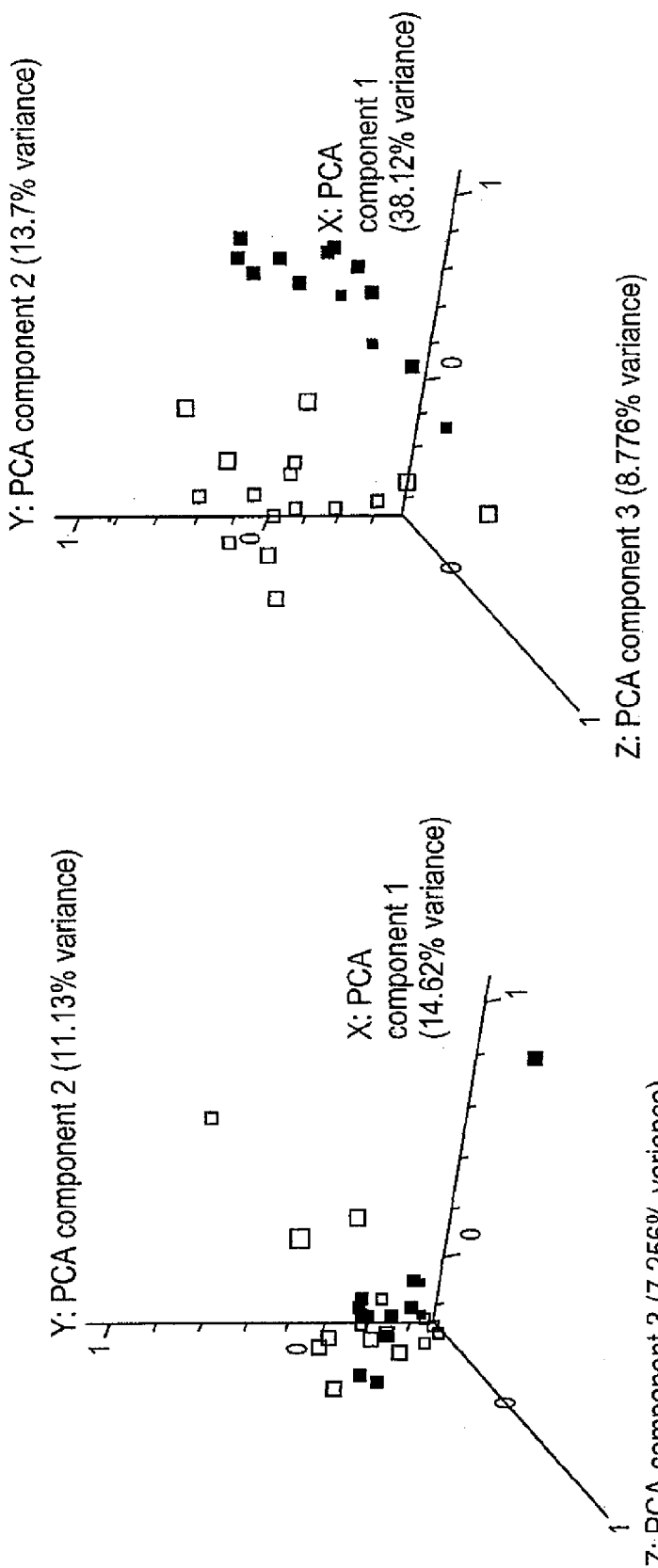

PROGNOSIS PREDICTION FOR MELANOMA CANCER

PRIORITY CLAIM

This application is a United States continuation application filed under 35 U.S.C. 1.111(a) of PCT/NZ2008/000118, filed 23 May 2008, which claims priority to New Zealand provisional patent application No: 555,363, filed 24 May 2007. Both of these applications are incorporated herein fully by reference.

RELATED APPLICATION

This application claims the benefit of New Zealand Provisional Patent Application No. 555363 filed 24 May 2007, which is incorporated by reference herein in its entirety.

FIELD OF THE INVENTION

This invention relates to methods and compositions for determining the prognosis of cancer, particularly melanoma, in a patient. Specifically, this invention relates to the use of genetic and proteomic markers for determining the prognosis of cancer, such as melanoma, based on prognostic signatures.

BACKGROUND OF THE INVENTION

In industrial nations, the incidence of melanoma has steadily risen over the previous 25 years, with the incidence in Australia being the highest in the world[1]. Although the perceived "melanoma epidemic" most probably represents increased detection of thin melanomas[2], melanoma affects predominantly younger age groups resulting in a loss of productive-life years exceeded only by childhood malignancies and testicular cancer[3,4]. Melanoma is largely unresponsive to cytotoxic chemotherapy[5], biological agents[6,7] and various vaccination strategies[8]. A small subgroup of patients appear to benefit from biological and/or cytotoxic chemotherapies, but identifying these patients a priori is currently impossible, which necessitates the exposure of many patients to substantial toxicities with a low probability of benefit.

Once melanoma has metastasized to local lymph nodes, 70% of patients will die within 5 years[9]. The sub-group of patients with prolonged survival represents a unique cohort. No current adjuvant therapies offer an overall survival benefit, and while some clinicians offer interferon-α to improve disease-free survival[10], many international centers offer no active adjuvant treatment outside clinical trials. Predicting which patients are likely to do well regardless of the use of adjuvant therapies would prevent needless toxicity, and enable the development of better therapeutic strategies targeting those more likely to obtain benefit. Better stratification of patients in adjuvant clinical trials will reduce both type I and type II errors. The 12 year update following the ECOG 1684 study and other randomized studies have demonstrated that interferon-α improves TTP but not overall survival in stage III melanoma[5,10,11]. Inherent heterogeneity within the patient populations, which are now well recognized but unable to be controlled for, may have confounded the promising effects on survival seen in the initial ECOG 1684 study[10]) and other smaller phase II studies. Stratifying those patients more likely to relapse may balance this heterogeneity and allow treatments to be compared more accurately.

There is a need for further tools to predict the prognosis of melanoma. This invention provides methods, compositions, kits, and devices based on prognostic cancer markers, specifically melanoma prognostic markers, to aid in the prognosis and treatment of cancer.

SUMMARY OF THE INVENTION

In certain embodiments there is provided a set of markers genes identified to be differentially expressed in melanomas with a good prognosis and melanomas with a poor prognosis. This set of genes can be used to generate prognostics signatures, comprising two or more markers, capable of predicting the speed of progression of melanoma in a patient.

The individual markers can be differentially expressed depending on whether the tumour progresses rapidly or not. The accuracy of prediction can be enhanced by combining the markers together into a prognostic signature, providing for much more effective individual tests than single-gene assays. Also provided for is the application of techniques, such as statistics, machine learning, artificial intelligence, and data mining to the prognostics signatures to generate prediction models. In another embodiment, expression levels of the markers of a particular prognostic signature in the tumour of a patient can then be applied to the prediction model to determine the prognosis.

In certain embodiments, the expression level of the markers can be established using microarray methods, quantitative polymerase chain reaction (qPCR), or immunoassays.

Specifically the present invention provides for a method for determining the prognosis of melanoma in a patient, comprising the steps of;
  (i) determining the expression level of a melanoma prognostic marker (MPM), or of a prognostic signature comprising two or more MPMs, in a melanoma tumour sample from the patient,
  (ii) applying a predictive model, established by applying a predictive method to expressions levels of the MPM or the predictive signature in prognostically good and poor tumour samples,
  (iii) establishing a prognosis.

Alternatively the present invention also provides for a method for determining the suitability of a melanoma patient for a drug trial, comprising the steps of;
  (i) determining the expression level of an MPM, or of a prognostic signature comprising two or more MPMs, in a melanoma tumour sample from the patient.
  (ii) applying a predictive model, established by applying a predictive method to expressions levels of the MPM or predictive signature in prognostically good and poor tumour samples,
  (iii) establishing the suitability of the patient to the trial.

The MPMs according to the methods can be selected from table 1. The predictive method is selected from the group consisting of linear models, support vector machines, neural networks, classification and regression trees, ensemble learning methods, discriminant analysis, nearest neighbor method, bayesian networks, independent components analysis.

Determining the expression level of a MPM or a prognostic signature can be carried out by detecting the expression level of mRNA of each gene, for example using qPCR method using a forward primer and a reverse primer. Determining the expression level of an MPM or a prognostic signature can also be carried out by detecting the expression level of cDNA of each gene, for example by using a nucleotide complementary to at least a portion of said cDNA, Further the expression level of an MPM or a prognostic signature can be determined by detecting the expression level of the protein of each marker, or by detecting the expression level of the peptide of each marker, for example by using an antibody directed against each marker, such as a monoclonal antibody or a polyclonal antiserum. A sandwich-type immunoassay method or ELISA assay could be used.

The present invention also provides for a prognostic signature for determining the risk of progression of melanoma, comprising two or more melanoma prognostic markers (MPMs). The MPMs of the prognostic signature can be selected from table 1.

In another aspect, the present invention provides for a device for determining prognosis of melanoma, comprising:
a substrate having one or more locations thereon, each location having two or more oligonucleotides thereon, each oligonucleotide selected from the one or more MPMs.

The two or more oligonucleotides can be MPMs selected from table 1.

The present invention also provides for the use of a reagent for detecting the expression of a MPM, or of a prognostic signature comprising two or more MPMs, in the manufacture of a kit for predicting the prognosis of melanoma in a patient. The MPMs can be selected from table 1.

The reagent can detect the level of expression of the one or more MPMs by detecting expression of MPM mRNA or MPM cDNA. The reagent can be an oligonucleotide complementary to at least a portion of the MPM mRNA or cDNA. Alternatively the reagent can detect the level of expression of the one or more MPMs by detecting expression of a MPM protein or peptide. The reagent can be an antibody, such as a monoclonal antibody of polyclonal antiserum.

The kit may be suitable for undertaking a sandwich-type immunoassay or an ELISA assay.

BRIEF DESCRIPTION OF THE FIGURES

This invention is described with reference to specific embodiments thereof and with reference to the figures, in which:

FIG. 1 depicts the 22 genes used to build predictive scores ("melanoma markers"). Genes were selected using a Mann-Whitney test.

FIG. 4 depicts RNA used to create the Reference cDNA used in both the array experiments and as a comparator in qPCR assays.

FIG. 5 depicts the assays used for qPCR using Universal Probe Library Probes.

FIG. 6 depicts the patient characteristics for the test set and validation set A.

FIG. 7 depicts Principal Components Analysis using all genes (A) and differentially expressed genes (B), demonstrating the ability of the 15 genes to segregate the good (filled boxes) from the poor (unfilled boxes) prognostic groups. These genes were used to develop the array and qPCR based predictors.

DETAILED DESCRIPTION

Definitions

Figure 2:
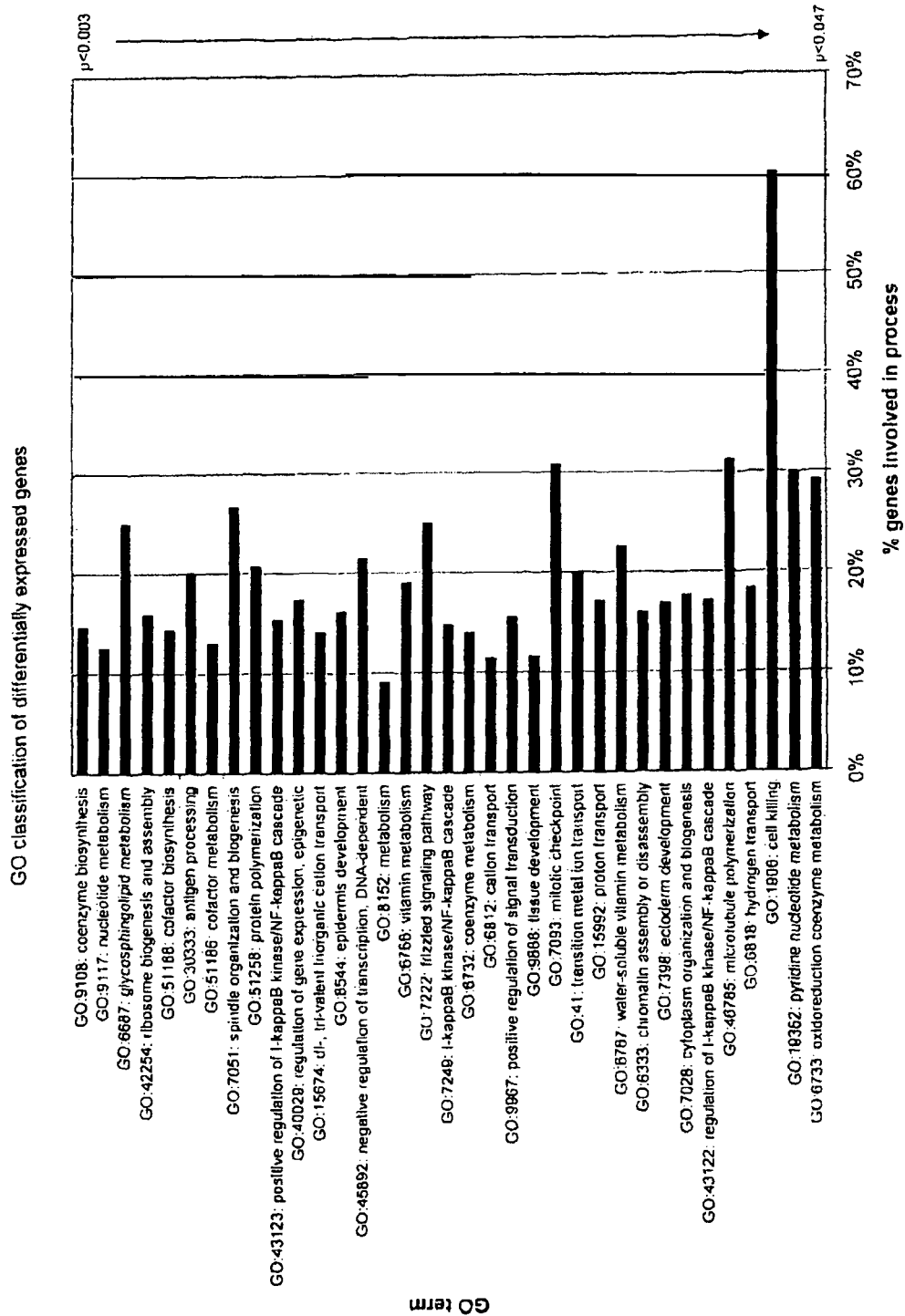
FIG. 2 depicts the Gene Ontology groupings of the differentially expressed genes and associated significance. The most significant ontologies are determined by the number of genes which overlap between categories i.e the likelihood that it is a co-incidence that this many genes were in both the gene list and the category.

Before describing embodiments of the invention in detail, it will be useful to provide some definitions of terms used herein.

The term "marker" refers to a molecule that is associated quantitatively or qualitatively with the presence of a biological phenomenon. Examples of "markers" include a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of the invention include the nucleotide sequences (e.g., GenBank sequences) as disclosed herein, in particular, the full-length sequences, any coding sequences, any fragments, or any complements thereof, and any measurable marker thereof as defined above.

The terms "MPM" or "melanoma prognostic marker" or "MPM family member" refer to a marker with altered expression that is associated with a particular prognosis, e.g., a higher or lower likelihood of a cancer progressing to a more advanced stage, as described herein, but can exclude molecules that are known in the prior art to be associated with prognosis of melanoma. It is to be understood that the term MPM does not require that the marker be specific only for melanomas. Rather, expression of an MPM can be altered in other types of tumours, including malignant tumours.

The terms "prognostic signature," "signature," and the like refer to a set of two or more markers, for example MPMs, that when analysed together as a set allow for the determination of or prediction of an event, for example the prognostic outcome of melanoma. The use of a signature comprising two or more markers reduces the effect of individual variation and allows for a more robust prediction. Non-limiting examples of MPMs are set fourth in XX. In the context of the present invention, reference to "at least one," "at least two," "at least five," etc., of the markers listed in any particular set (e.g., any signature) means any one or any and all combinations of the markers listed.

The term "prediction method" is defined to cover the broader genus of methods from the fields of statistics, machine learning, artificial intelligence, and data mining, which can be used to specify a prediction model. The term also includes any method suitable for predicting an outcome, and includes the methods of not only using complex analysis of multiple markers, but also the direct comparison of the expression of a single marker or signature to that of a control tissue, or to a predetermined threshold, in order to predict an outcome. These are discussed further in the Detailed Description section.

The term "prediction model" refers to the specific mathematical model obtained by applying a prediction method to a collection of data. In the examples detailed herein, such data sets consist of measurements of gene activity in tissue samples taken from melanoma patients with a good or poor prognosis, for which the class (good or poor) of each sample is known. Such models can be used to (1) classify a sample of unknown prognosis status as being one of good or poor, or (2) make a probabilistic prediction (i.e., produce either a proportion or percentage to be interpreted as a probability) which represents the likelihood that the unknown sample has a good prognosis, based on the measurement of mRNA expression levels or expression products, of a specified collection of genes, in the unknown sample. The exact details of how these gene-specific measurements are combined to produce classifications and probabilistic predictions are dependent on the specific mechanisms of the prediction method used to construct the model. The term also includes any model suitable for predicting an outcome, and includes the models not only using complex analysis of multiple markers, but also models involving the direct comparison of the expression of a single marker or signature to that of a control tissue, or to a predetermined threshold, in order to predict an outcome.

"Sensitivity", "specificity" (or "selectivity"), and "classification rate", when applied to describing the effectiveness of prediction models mean the following:

"Sensitivity" means the proportion of truly positive samples that are also predicted (by the model) to be positive. In a test for prognosis of melanoma, that would be the proportion of tumours that have a good prognosis predicted by the model to be good. "Specificity" or "selectivity" means the proportion of truly negative samples that are also predicted (by the model) to be negative. In a test for the prognosis of melanoma, this equates to the proportion of samples that have a poor prognosis that are predicted to by poor by the model. "Classification Rate" is the proportion of all samples that are correctly classified by the prediction model (be that as positive or negative).

As used herein "antibodies" and like terms refer to immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., a mouse or human sequence. Further included are camelid antibodies, shark antibodies or nanobodies.

The terms "cancer" and "cancerous" refer to or describe the physiological condition in mammals that is typically characterized by abnormal or unregulated cell growth. Cancer and cancer pathology can be associated, for example, with metastasis, interference with the normal functioning of neighbouring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. Specifically included are melanomas.

The term "melanoma" refers to a tumor originating from melanocytes which are found in skin but also other sites such as oral and anogenital mucosal surfaces, esophagus, meninges and the eye. These tumors are able to metastasize to any organ.

The terms "differentially expressed," "differential expression," and like phrases, refer to a gene marker whose expression is activated to a higher or lower level in a subject (e.g., test sample) having a condition, specifically cancer, such as melanoma, relative to its expression in a control subject (e.g., reference sample). The terms also include markers whose expression is activated to a higher or lower level at different stages of the same condition; in diseases with a good or poor prognosis; or in cells with higher or lower levels of proliferation. A differentially expressed marker may be either activated or inhibited at the polynucleotide level or polypeptide level, or may be subject to alternative splicing to result in a different polypeptide product. Such differences may be evidenced by a change in mRNA levels, surface expression, secretion or other partitioning of a polypeptide, for example.

Differential expression may include a comparison of expression between two or more markers (e.g., genes or their gene products); or a comparison of the ratios of the expression between two or more markers (e.g., genes or their gene products); or a comparison of two differently processed products (e.g., transcripts or polypeptides) of the same marker, which differ between normal subjects and diseased subjects; or between various stages of the same disease; or between diseases having a good or poor prognosis; or between cells with higher and lower levels of proliferation; or between normal tissue and diseased tissue, specifically cancer, or melanoma. Differential expression includes both quantitative, as well as qualitative, differences in the temporal or cellular expression pattern in a gene or its expression products among, for example, normal and diseased cells, or among cells which have undergone different disease events or disease stages, or cells with different levels of proliferation.

The term "expression" includes production of polynucleotides and polypeptides, in particular, the production of RNA (e.g., mRNA) from a gene or portion of a gene, and includes the production of a polypeptide encoded by an RNA or gene or portion of a gene, and the appearance of a detectable material associated with expression. For example, the formation of a complex, for example, from a polypeptide-polypeptide interaction, polypeptide-nucleotide interaction, or the like, is included within the scope of the term "expression". Another example is the binding of a binding ligand, such as a hybridization probe or antibody, to a gene or other polynucleotide or oligonucleotide, a polypeptide or a protein fragment, and the visualization of the binding ligand. Thus, the intensity of a spot on a microarray, on a hybridization blot such as a Northern blot, or on an immunoblot such as a Western blot, or on a bead array, or by PCR analysis, is included within the term "expression" of the underlying biological molecule.

The terms "expression threshold," and "defined expression threshold" are used interchangeably and refer to the level of a marker in question outside which the polynucleotide or polypeptide serves as a predictive marker for patient survival. The threshold will be dependent on the predictive model established are derived experimentally from clinical studies such as those described in the Examples below. Depending on the prediction model used, the expression threshold may be set to achieve maximum sensitivity, or for maximum specificity, or for minimum error (maximum classification rate). For example a higher threshold may be set to achieve minimum errors, but this may result in a lower sensitivity. Therefore, for any given predictive model, clinical studies will be used to set an expression threshold that generally achieves the highest sensitivity while having a minimal error rate. The determination of the expression threshold for any situation is well within the knowledge of those skilled in the art.

The term "long-term survival" is used herein to refer to survival for at least 5 years, more preferably for at least 8 years, most preferably, for at least 10 years following surgery or other treatment.

The term "microarray" refers to an ordered or unordered arrangement of capture agents, preferably polynucleotides (e.g., probes) or polypeptides on a substrate. See, e.g., Microarray Analysis, M. Schena, John Wiley & Sons, 2002; Microarray Biochip Technology, M. Schena, ed., Eaton Publishing, 2000; Guide to Analysis of DNA Microarray Data, S. Knudsen, John Wiley & Sons, 2004; and Protein Microarray Technology, D. Kambhampati, ed., John Wiley & Sons, 2004.

The term "oligonucleotide" refers to a polynucleotide, typically a probe or primer, including, without limitation, single-stranded deoxyribonucleotides, single- or double-stranded ribonucleotides, RNA: DNA hybrids, and double-stranded DNAs. Oligonucleotides, such as single-stranded DNA probe oligonucleotides, are often synthesized by chemical methods, for example using automated oligonucleotide synthesizers that are commercially available, or by a variety of other methods, including in vitro expression systems, recombinant techniques, and expression in cells and organisms.

The term "polynucleotide," when used in the singular or plural, generally refers to any polyribonucleotide or polydeoxribonucleotide, which may be unmodified RNA or DNA or modified RNA or DNA. This includes, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences. It will be understood that each reference to a "polynucleotide" or like term, herein, will include the full-length sequences as well as any fragments, derivatives, or variants thereof.

"Polypeptide," as used herein, refers to an oligopeptide, peptide, or protein sequence, or fragment thereof, and to naturally occurring, recombinant, synthetic, or semi-synthetic molecules. Where "polypeptide" is recited herein to refer to an amino acid sequence of a naturally occurring protein molecule, "polypeptide" and like terms, are not meant to limit the amino acid sequence to the complete, native amino acid sequence for the full-length molecule. It will be understood that each reference to a "polypeptide" or like term, herein, will include the full-length sequence, as well as any fragments, derivatives, or variants thereof.

The term "prognosis" refers to a prediction of medical outcome, for example, a poor or good outcome (e.g., likelihood of long-term survival); a negative prognosis, or poor outcome, includes a prediction of relapse, disease progression (e.g., tumour growth or metastasis, or drug resistance), or mortality; a positive prognosis, or good outcome, includes a prediction of disease remission, (e.g., disease-free status), amelioration (e.g., tumour regression), or stabilization.

The term "proliferation" refers to the processes leading to increased cell size or cell number, and can include one or more of: tumour or cell growth, angiogenesis, innervation, and metastasis.

The term "qPCR" or "QPCR" refers to quantative polymerase chain reaction as described, for example, in PCR Technique: Quantitative PCR, J. W. Larrick, ed., Eaton Publishing, 1997, and A-Z of Quantitative PCR, S. Bustin, ed., IUL Press, 2004.

The term "tumour" refers to all neoplastic cell growth and proliferation, whether malignant or benign, and all pre-cancerous and cancerous cells and tissues.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridisable sequence, the higher the relative temperature which can be used. As a result, it follows that higher relative temperatures would tend to make the reaction conditions more stringent, while lower temperatures less so. Additional details and explanation of stringency of hybridization reactions, are found e.g. in Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×, Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash comprising 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, 2nd edition. Sambrook et al., 1989; Oligonucleotide Synthesis, M J Gait, ed., 1984; Animal Cell Culture, R. I. Freshney, ed., 1987; Methods in Enzymology, Academic Press, Inc.; Handbook of Experimental Immunology, 4th edition, D. M. Weir & C C. Blackwell, eds., Blackwell Science Inc., 1987; Gene Transfer Vectors for Mammalian Cells, J. M. Miller & M. P. Calos, eds., 1987; Current Protocols in Molecular Biology, F. M. Ausubel et al., eds., 1987; and PCR: The Polymerase Chain Reaction, Mullis et al., eds., 1994.

DESCRIPTION OF EMBODIMENTS OF THE INVENTION

The present invention discloses the use of microarrays to identify and determine the specific prognostic role of specific prognostic markers and signatures in melanoma. The microarray-based studies shown herein establish markers that can be used to predict, a good or poor prognosis for a patient with melanoma. In particular the microarray-based studies and qPCR analysis shown herein indicate that particular differentially expressed genes can be used as prognostic signatures that are associated with a particular prognosis. The invention can therefore be used to identify patients who are likely to have aggressive disease.

The present invention provides for markers for the determination of disease prognosis. Using the methods of the invention, it has been found, that markers are associated with the prognosis of melanoma, and can be used to predict outcome. Microarray analysis of samples taken from patients with various stages of melanoma has led to the surprising discovery that specific patterns of marker expression are associated with prognosis of the cancer. The present invention therefore provides for a set of genes, outlined in Table 1, that are differentially expressed in melanomas with a good or poor outcome. The genes outlined in Table 1 provide for a set of melanoma prognostic markers (MPMs).

A decrease in certain melanoma prognostic markers (MPMs), for example, can be indicative of a particular prognosis. Conversely, an increase in other MPMs is indicative of a particular prognosis. A particular prognosis can include the speed of disease progression. A decrease or increase in expression can be determined, for example, by comparison of a test sample, e.g., patient's tumour sample, to a reference sample, e.g., a sample associated with a known prognosis. In particular, one or more samples from patient(s) with a good prognosis could be used as a reference sample.

For example, to obtain a prognosis, expression levels in a patient's sample (e.g., tumour sample) can be compared to samples from patients with a known outcome. If the patient's sample shows increased or decreased expression of one or more MPMs that compares to samples with poor outcome (a rapid disease progression), then a poor prognosis is implicated. If the patient's sample shows expression of one or more MPMs that is comparable to samples with good outcome (a slow disease progression) then a positive prognosis, or good prognosis, is implicated.

As further examples, the expression levels of a prognostic signature comprising two or more MPMs from a patient's sample (e.g., tumour sample) can be compared to samples of cancers known to have good or poor prognosis. If the patient's sample shows increased or decreased expression of MPMs by comparison to samples with good prognosis, and/or comparable expression to samples of poor prognosis, then a negative prognosis is implicated. If the patient's sample shows expression of MPMs that is comparable to samples of a good prognosis, and/or lower or higher expression than samples with a poor prognosis, then a positive, or good, prognosis is implicated.

As one approach, a prediction method can be applied to a panel of markers, for example the panel of MPMs outlined in Table 1, in order to generate a predictive model. This involves the generation of a prognostic signature, comprising two or more MPMs.

The disclosed MPMs in Table 1 therefore provide a useful set of markers to generate prediction signatures for determining the prognosis of cancer, and establishing a treatment regime, or treatment modality, specific for that tumour. In particular, a positive prognosis can be used by a patient to decide to pursue particular treatment options. A negative prognosis can be used by a patient to decide to terminate treatment or to pursue highly aggressive or experimental treatments. In addition, a patient can chose treatments based on their prognosis predicted from the expression of prognostic markers (e.g., MPMs).

Levels of MPMs can be detected in tumour tissue, tissue proximal to the tumour, lymph node samples, blood samples, serum samples, urine samples, or faecal samples, using any suitable technique, and can include, but is not limited to, oligonucleotide probes, quantitative PCR, or antibodies raised against the markers. It will be appreciated that by analyzing the presence and amounts of expression of a plurality of MPMs in the form of prediction signatures, and constructing a prognostic signature, the sensitivity and accuracy of prognosis will be increased. Therefore, multiple markers according to the present invention can be used to determine the prognosis of a cancer.

The invention includes the use of archived paraffin-embedded biopsy material for assay of the markers in the set, and therefore is compatible with the most widely available type of biopsy material. It is also compatible with several different methods of tumour tissue harvest, for example, via core biopsy or fine needle aspiration. In certain aspects, RNA is isolated from a fixed, wax-embedded cancer tissue specimen of the patient. Isolation may be performed by any technique known in the art, for example from core biopsy tissue or fine needle aspirate cells.

In one aspect, the invention relates to a method of predicting a prognosis, e.g., the likelihood of long-term survival of a cancer patient following treatment, comprising determining the expression level of one or more prognostic markers or their expression products in a sample obtained from the patient, normalized against the expression level of other RNA transcripts or their products in the sample, or of a reference set of RNA transcripts or their expression products.

In specific aspects, the prognostic marker is one or more markers listed in Table 1, or is included as one or more of the prognostic signatures derived from the markers listed in Table 1.

In further aspects, the expression levels of the prognostic markers or their expression products are determined, e.g., for the markers listed in Table 1 and a prognostic signature derived from the markers listed in Table 1. In another aspect, the method comprises the determination of the expression levels of a full set of prognosis markers or their expression products, e.g. for the markers listed in Table 1, or, a prognostic signature derived from the markers listed in Table 1.

In an additional aspect, the invention relates to an array (e.g., microarray) comprising polynucleotides hybridizing to two or more markers, e.g., for the markers listed in Table 1, or a prognostic signature derived from the markers listed in Table 1. In particular aspects, the array comprises polynucleotides hybridizing to prognostic signature derived from the markers listed in Table 1. In another specific aspect, the array comprises polynucleotides hybridizing to the full set of markers, e.g., for the markers listed in Table 1.

For these arrays, the polynucleotides can be cDNAs, or oligonucleotides, and the solid surface on which they are displayed can be glass, for example. The polynucleotides can hybridize to one or more of the markers as disclosed herein, for example, to the full-length sequences, any coding sequences, any fragments, or any complements thereof. In particular aspects, an increase or decrease in expression levels of one or more MPM indicates a decreased likelihood of long-term survival. e.g., due to cancer recurrence, while a lack of an increase or decrease in expression levels of one or more MPM indicates an increased likelihood of long-term survival without cancer recurrence.

expression (SAGE; Velculescu et al., Science 270: 484-487 (1995); and Velculescu et al. Cell 88: 243-51 (1997)), MassARRAY technology (Sequenom, San Diego, Calif.), and gene expression analysis by massively parallel signature sequencing (MPSS; Brenner et al., Nature Biotechnology 18: 630-634 (2000)). Alternatively, antibodies may be employed that can recognize specific complexes, including DNA duplexes, RNA duplexes, and DNA-RNA hybrid duplexes or DNA-polypeptide duplexes.

Primary data can be collected and fold change analysis can be performed, for example, by comparison of marker expression levels in tumour tissue and non-tumour tissue; by comparison of marker expression levels to levels determined in recurring tumours and non-recurring tumours; by comparison of marker expression levels to levels determined in tumours

TABLE 1

Melanoma Predictive Markers

| Description | P-value | Common | Genbank |
|---|---|---|---|
| Thioredoxin domain containing 5 | 0.049 | TXNDC5 | NM_030810 |
| Paired immunoglobin-like type 2 receptor alpha | 0.049 | PILRA | NM_013439 |
| Major histocompatibility complex, class I, E | 0.049 | HLA-E | NM_005516 |
| kiaa1067; kiaa1067 | 0.049 | | XM_036173 |
| Inosine triphosphatase (nucleoside triphosphate pyrophosphatase) | 0.049 | ITPA | NM_033453 |
| Desmuslin* | 0.0482 | DMN | NM_145728 |
| GTP binding protein 2 | 0.0429 | GTPBP2 | NM_019096 |
| Milk fat globule-EGF factor 8 protein | 0.0429 | MFGE8 | NM_005928 |
| Isocitrate dehydrogenase 1 (NADP+), soluble | 0.0365 | IDH1 | NM_005896 |
| Mitochondrial ribosomal protein S5 | 0.0365 | MRPS5 | NM_031902 |
| Lectin, galactoside-binding, soluble, 7 (galectin 7) | 0.0307 | LGALS7 | NM_002307 |
| Kv channel interacting protein 2 | 0.0295 | KCNIP2 | AF347114 |
| Carbohydrate (N-acetylglucosamine 6-O) sulfotransferase 4 | 0.0235 | CHST4 | NM_005769 |
| ensembl genscan prediction | 0.0295 | | AL451139.11.67295.95669.1 |
| Human phosphotyrosine independent ligand | 0.023 | OSIL; A170; p62B | U46752 |
| Nuclear factor of kappa light polypeptide gene enhancer in B-cells inhibitor, beta | 0.023 | NFKBIB | NM_002503 |
| Mitochondrial carrier homolog 2 (*C. elegans*) | 0.023 | MTCH2 | NM_014342 |
| ADP-ribosylation factor related protein 1 | 0.0136 | ARFRP1 | NM_003224 |
| birch pollen allergen specific immunoglobulin gamma chain** | 0.0136 | BABI-L | AJ131063 |
| Tubulin alpha 1b*** | 0.0136 | TUBA1B | NM_006082 |
| partial n-myc exon 3 | 0.00371 | | AJ242956_2 |
| Plexin B2 | 0.000756 | PLXNB2 | AB002313 |

*This marker was previously known as kiaa0353; dmn (XM_031031).
**This marker was previously known as Immunoglobulin kappa variable 1-5 (IGKC; AJ131063).
***This marker was previously known as similar to tubulin alpha 6; loc143712 (XM_084610).

General Approaches to Prognostic Marker Detection

The following approaches are non-limiting methods that can be used to detect the proliferation markers, including MPM family members: microarray approaches using oligonucleotide probes selective for a MPM; real-time qPCR on tumour samples using MPM specific primers and probes; real-time qPCR on lymph node, blood, serum, faecal, or urine samples using MPM specific primers and probes; enzyme-linked immunological assays (ELISA); immunohistochemistry using anti-marker antibodies; and analysis of array or qPCR data using computers.

Other useful methods include northern blotting and in situ hybridization (Parker and Barnes, Methods in Molecular Biology 106: 247-283 (1999)); RNase protection assays (Hod, BioTechniques 13: 852-854 (1992)); reverse transcription polymerase chain reaction (RT-PCR; Weis et al., Trends in Genetics 8: 263-264 (1992)); serial analysis of gene with or without metastasis; by comparison of marker expression levels to levels determined in differently staged tumours; or by comparison of marker expression levels to levels determined in cells with different levels of proliferation. A negative or positive prognosis is determined based on this analysis. Further analysis of tumour marker expression includes matching those markers exhibiting increased or decreased expression with expression profiles of known melanoma tumours to provide a prognosis.

A threshold for concluding that expression is increased will be dependent on the particular marker and also the particular predictive model that is to be applied. The threshold is generally set to achieve the highest sensitivity and selectivity with the lowest error rate, although variations may be desirable for a particular clinical situation. The desired threshold is determined by analysing a population of sufficient size taking into account the statistical variability of any predictive model and is calculated from the size of the sample used to produce the predictive model. The same applies for the determination of a threshold for concluding that expression is decreased. It can be appreciated that other thresholds, or methods for establishing a threshold, for concluding that increased or decreased expression has occurred can be selected without departing from the scope of this invention.

It is also possible that a prediction model may produce as it's output a numerical value, for example a score, likelihood value or probability. In these instances, it is possible to apply thresholds to the results produced by prediction models, and in these cases similar principles apply as those used to set thresholds for expression values.

Once the expression level, or output of a prediction model, of a predictive signature in a tumour sample has been obtained, the likelihood of the cancer recurring can then be determined.

From the markers identified, prognostic signatures comprising one or more MPMs can be used to determine the prognosis of a cancer, by comparing the expression level of the one or more markers to the disclosed prognostic signature. By comparing the expression of one or more of the MPMs in a tumour sample with the disclosed prognostic signature, the likelihood of the cancer recurring can be determined. The comparison of expression levels of the prognostic signature to establish a prognosis can be done by applying a predictive model as described previously.

Determining the likelihood of the cancer recurring is of great value to the medical practitioner. A high likelihood a tumour not responding to treatment means that a longer or higher dose treatment should be considered or treatment may not be given at all. An accurate prognosis is also of benefit to the patient. It allows the patient, along with their partners, family, and friends to also make decisions about treatment, as well as decisions about their future and lifestyle changes. Therefore, the invention also provides for a method establishing a treatment regime for a particular cancer based on the prognosis established by matching the expression of the markers in a tumour sample with the differential expression signature.

It will be appreciated that the marker selection, or construction of a prognostic signature, does not have to be restricted to the MPMs disclosed in Table 1 herein, but could involve the use of one or more MPMs from the disclosed signatures, or a new signature may be established using MPMs selected from the disclosed marker lists. The requirement of any signature is that it predicts the likelihood of rapid disease progression with enough accuracy to assist a medical practitioner to establish a treatment regime.

Reverse Transcription PCR (RT-PCR)

Of the techniques listed above, the most sensitive and most flexible quantitative method is RT-PCR, which can be used to compare RNA levels in different sample populations, in normal and tumour tissues, with or without drug treatment, to characterize patterns of expression, to discriminate between closely related RNAs, and to analyze RNA structure.

For RT-PCR, the first step is the isolation of RNA from a target sample. The starting material is typically total RNA isolated from human tumours or tumour cell lines, and corresponding normal tissues or cell lines, respectively. RNA can be isolated from a variety of samples, such as tumour samples from breast, lung, colon (e.g., large bowel or small bowel), skin, colorectal, gastric, esophageal, anal, rectal, prostate, brain, liver, kidney, pancreas, spleen, thymus, testis, ovary, uterus, etc., tissues, from primary tumours, or tumour cell lines, and from pooled samples from healthy donors. If the source of RNA is a tumour, RNA can be extracted, for example, from frozen or archived paraffin-embedded and fixed (e.g., formalin-fixed) tissue samples.

The first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukaemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man (q) PCR typically utilizes the 5' nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipment, such as, for example, ABI PRISM 7700 Sequence Detection System (Perkin-Elmer-Applied Biosystems, Foster City, Calif., USA), or Lightcycler (Roche Molecular Biochemicals. Mannheim, Germany). In a preferred embodiment, the 5' nuclease procedure is run on a real-time quantitative PCR device such as the ABI PRISM 7700tam Sequence Detection System. The system consists of a thermocycler, laser, charge-coupled device (CCD), camera, and computer. The system amplifies samples in a 96-well format on a thermocycler. During amplification, laser-induced fluorescent signal is collected in real-time through fibre optics cables for all 96 wells, and detected at the CCD. The system includes software for running the instrument and for analyzing the data.

5' nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and-actin.

Real-Time Quantitative PCR (qPCR)

A more recent variation of the RT-PCR technique is the real time quantitative PCR, which measures PCR product accumulation through a dual-labeled fluorigenic probe (i.e., TaqMan probe). Real time PCR is compatible both with quantitative competitive PCR and with quantitative comparative PCR. The former uses an internal competitor for each target sequence for normalization, while the latter uses a normalization gene contained within the sample, or a housekeeping gene for RT-PCR. Further details are provided, e.g., by Held et al., Genome Research 6: 986-994 (1996).

Expression levels can be determined using fixed, paraffin-embedded tissues as the RNA source. According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., Genome Res. 12 (4): 656-64 (2002), or by the BLAST software including its variations. Subsequent steps follow well established methods of PCR primer and probe design.

In order to avoid non-specific signals, it is useful to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers in: Krawetz S, Misener S (eds) Bioinformatics Methods and Protocols: Methods in Molecular Biology. Humana Press, Totowa, N.J., pp 365-386).

The most important factors considered in PCR primer design include primer length, melting temperature ($T_m$), and G/C content, specificity, complementary primer sequences, and 3' end sequence. In general, optimal PCR primers are generally 17-30 bases in length, and contain about 20-80%, such as, for example, about 50-60% G+C bases. Melting temperatures between 50 and 80° C., e.g., about 50 to 70° C., are typically preferred. For further guidelines for PCR primer and probe design see, e.g., Dieffenbach, C. W. et al., General Concepts for PCR. Primer Design in: PCR Primer, A Laboratory Manual, Cold Spring Harbor Laboratory Press, New York, 1995, pp. 133-155; Innis and Gelfand, Optimization of PCRs in: PCR Protocols, A Guide to Methods and Applications, CRC Press, London, 1994, pp. 5-11; and Plasterer, T. N. Primerselect: Primer and probe design. Methods Mol. Biol. 70: 520-527 (1997), the entire disclosures of which are hereby expressly incorporated by reference.

Microarray Analysis

Differential expression can also be identified, or confirmed using the microarray technique. Thus, the expression profile of MPMs can be measured in either fresh or paraffin-embedded tumour tissue, using microarray technology. In this method, polynucleotide sequences of interest (including cDNAs and oligonucleotides) are plated, or arrayed, on a microchip substrate. The arrayed sequences (i.e., capture probes) are then hybridized with specific polynucleotides from cells or tissues of interest (i.e., targets). Just as in the RT-PCR method, the source of RNA typically is total RNA isolated from human tumours or tumour cell lines, and corresponding normal tissues or cell lines. Thus RNA can be isolated from a variety of primary tumours or tumour cell lines. If the source of RNA is a primary tumour, RNA can be extracted, for example, from frozen or archived formalin fixed paraffin-embedded (FFPE) tissue samples and fixed (e.g., formalin-fixed) tissue samples, which are routinely prepared and preserved in everyday clinical practice.

In a specific embodiment of the microarray technique, PCR amplified inserts of cDNA clones are applied to a substrate. The substrate can include up to 1, 2, 5, 10, 15, 20, 25, 30, 35, 40, 45, 50, or 75 nucleotide sequences, In other aspects, the substrate can include at least 10,000 nucleotide sequences. The microarrayed sequences, immobilized on the microchip, are suitable for hybridization under stringent conditions. As other embodiments, the targets for the microarrays can be at least 50, 100, 200, 400, 500, 1000, or 2000 bases in length; or 50-100, 100-200, 100-500, 100-1000, 100-2000, or 500-5000 bases in length. As further embodiments, the capture probes for the microarrays can be at least 10, 15, 20, 25, 50, 75, 80, or 100 bases in length; or 10-15, 10-20, 10-25, 10-50, 10-75, 10-80, or 20-80 bases in length.

Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual colour fluorescence, separately labeled cDNA probes generated from two sources of RNA are hybridized pairwise to the array. The relative abundance of the transcripts from the two sources corresponding to each specified gene is thus determined simultaneously.

The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93 (2): 106-149 (1996)). Microarray analysis can be performed by commercially available equipment, following manufacturer's protocols, such as by using the Affymetrix GenChip technology, Illumina microarray technology or Incyte's microarray technology. The development of microarray methods for large-scale analysis of gene expression makes it possible to search systematically for molecular markers of cancer classification and outcome prediction in a variety of tumour types.

RNA Isolation, Purification, and Amplification

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56: A67 (1987), and De Sandres et al., BioTechniques 18: 42044 (1995). In particular, RNA isolation can be performed using purification kit, buffer set, and protease from commercial manufacturers, such as Qiagen, according to the manufacturer's instructions. For example, total RNA from cells in culture can be isolated using Qiagen RNeasy mini-columns Other commercially available RNA isolation kits include Master-Pure Complete DNA and RNA Purification Kit (EPICENTRE (D, Madison, Wis.), and Paraffin Block RNA Isolation Kit (Ambion, Inc.). Total RNA from tissue samples can be isolated using RNA Stat-60 (Tel-Test). RNA prepared from a tumour can be isolated, for example, by cesium chloride density gradient centrifugation.

The steps of a representative protocol for profiling gene expression using fixed, paraffin-embedded tissues as the RNA source, including mRNA isolation, purification, primer extension and amplification are given in various published journal articles (for example: T. E. Godfrey et al. J. Molec. Diagnostics 2: 84-91 (2000); K. Specht et al., Am. J. Pathol. 158: 419-29 (2001)). Briefly, a representative process starts with cutting about 10 μm thick sections of paraffin-embedded tumour tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumour sample examined.

Immunohistochemistry and Proteomics

Immunohistochemistry methods are also suitable for detecting the expression levels of the proliferation markers of the present invention. Thus, antibodies or antisera, preferably polyclonal antisera, and most preferably monoclonal antibodies specific for each marker, are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomics can be used to analyze the polypeptides present in a sample (e.g., tissue, organism, or cell culture) at a certain point of time. In particular, proteomic techniques can be used to assess the global changes of polypeptide expression in a sample (also referred to as expression proteomics). Proteomic analysis typically includes: (1) separation of individual polypeptides in a sample by 2-D gel electrophoresis (2-D PAGE); (2) identification of the individual polypeptides recovered from the gel, e.g., by mass spectrometry or N-terminal sequencing, and (3) analysis of the data using bioinformatics. Proteomics methods are valuable supplements to other methods of gene expression profiling, and can be used, alone or in combination with other methods, to detect the products of the proliferation markers of the present invention.

Once the expression level of one or more prognostic markers in a tumour sample has been assessed the likelihood of the cancer responding to treatment can then be determined. The inventors have identified a number of markers that are differentially expressed in melanomas that respond to treatment (good prognosis) compared to melanomas that don't respond to treatment (poor prognosis) in patient data sets. The markers are set out in Table 1 and in the example below.

Selection of Differentially Expressed Genes.

An early approach to the selection of genes deemed significant involved simply looking at the "fold change" of a given gene between the two groups of interest. While this approach hones in on genes that seem to change the most spectacularly, consideration of basic statistics leads one to realize that if the variance (or noise level) is quite high (as is often seen in microarray experiments), then seemingly large fold-change can happen frequently by chance alone.

Microarray experiments, such as those described here, typically involve the simultaneous measurement of thousands of genes. If one is comparing the expression levels for a particular gene between two groups (for example good prognosis and poor prognosis tumours), the typical tests for significance (such as the t-test) are not adequate. This is because, in an ensemble of thousands of experiments (in this context each gene constitutes an "experiment"), the probability of at least one experiment passing the usual criteria for significance by chance alone is essentially unity. In a test for significance, one typically calculates the probability that the "null hypothesis" is correct. In the case of comparing two groups, the null hypothesis is that there is no difference between the two groups. If a statistical test produces a probability for the null hypothesis below some threshold (usually 0.05 or 0.01), it is stated that we can reject the null hypothesis, and accept the hypothesis that the two groups are significantly different. Clearly, in such a test, a rejection of the null hypothesis by chance alone could be expected 1 in 20 times (or 1 in 100). The use of t-tests, or other similar statistical tests for significance, fail in the context of microarrays, producing far too many false positives (or type I errors).

In this type of situation, where one is testing multiple hypotheses at the same time, one applies typical multiple comparison procedures, such as the Bonferroni Method[12]. However such tests are too conservative for most microarray experiments, resulting in too many false negative (type II) errors.

A more recent approach is to do away with attempting to apply a probability for a given test being significant, and establish a means for selecting a subset of experiments, such that the expected proportion of Type I errors (or false discovery rate;[13]) is controlled for. It is this approach that has been used in this investigation, through various implementations; namely the methods provided with BRB Array Tools[14], and the limma[15,16] package of Bioconductor (that uses the R statistical environment;[17,18]).

General Methodology for Data Mining: Generation of Prognostic Signatures

Data Mining is the term used to describe the extraction of "knowledge", in other words the "know-how", or predictive ability from (usually) large volumes of data (the dataset). This is the approach used in this study to generate prognostic signatures. In the case of this study the "know-how" is the ability to accurately predict prognosis from a given set of gene expression measurements, or "signature" (as described generally in this section and in more detail in the examples section).

The specific details used for the methods used in this study are described in Examples 17-20. However, application of any of the data mining methods (both those described in the Examples, and those described here) can follow this general protocol.

Data mining[19], and the related topic machine learning[20] is a complex, repetitive mathematical task that involves the use of one or more appropriate computer software packages (see below). The use of software is advantageous on the one hand, in that one does not need to be completely familiar with the intricacies of the theory behind each technique in order to successfully use data mining techniques, provided that one adheres to the correct methodology. The disadvantage is that the application of data mining can often be viewed as a "black box": one inserts the data and receives the answer. How this is achieved is often masked from the end-user (this is the case for many of the techniques described, and can often influence the statistical method chosen for data mining. For example, neural networks and support vector machines have a particularly complex implementation that makes it very difficult for the end user to extract out the "rules" used to produce the decision. On the other band, k-nearest neighbours and linear discriminant analysis have a very transparent process for decision making that is not hidden from the user.

There are two types of approach used in data mining: supervised and unsupervised approaches. In the supervised approach, the information that is being linked to the data is known, such as categorical data (e.g. good vs. poor prognosis). What is required is the ability to link the observed response (e.g. good vs. poor prognosis) to the input variables. In the unsupervised approach, the classes within the dataset are not known in advance, and data mining methodology is employed to attempt to find the classes or structure within the dataset.

In the present example the supervised approach was used and is discussed in detail here, although it will be appreciated that any of the other techniques could be used.

The overall protocol involves the following steps:

Data representation. This involves transformation of the data into a form that is most likely to work successfully with the chosen data mining technique. In where the data is numerical, such as in this study where the data being investigated represents relative levels of gene expression, this is fairly simple. If the data covers a large dynamic range (i.e. many orders of magnitude) often the log of the data is taken. If the data covers many measurements of separate samples on separate days by separate investigators, particular care has to be taken to ensure systematic error is minimised. The minimisation of systematic error (i.e. errors resulting from protocol differences, machine differences, operator differences and other quantifiable factors) is the process referred to here as "normalisation".

Feature Selection. Typically the dataset contains many more data elements than would be practical to measure on a day-to-day basis, and additionally many elements that do not provide the information needed to produce a prediction model. The actual ability of a prediction model to describe a dataset is derived from some subset of the full dimensionality of the dataset. These dimensions are the most important components (or features) of the dataset. Note in the context of microarray data, the dimensions of the dataset are the individual genes. Feature selection, in the context described here, involves finding those genes which are most "differentially expressed". In a more general sense, it involves those groups which pass some statistical test for significance, i.e. is the level of a particular variable consistently higher or lower in one or other of the groups being investigated. Sometimes the features are those variables (or dimensions) which exhibit the greatest variance.

The application of feature selection is completely independent of the method used to create a prediction model, and involves a great deal of experimentation to achieve the desired results. Within this invention, the selection of significant genes, entailed feature selection. In addition, methods of data reduction (such as principal component analysis) can be applied to the dataset.

Training. Once the classes (e.g. good/poor prognosis) and the features of the dataset have been established, and the data is represented in a form that is acceptable as input for data mining, the reduced dataset (as described by the features) is applied to the prediction model of choice. The input for this model is usually in the form a multi-dimensional numerical input, (known as a vector), with associated output information (a class label or a response). In the training process, selected data is input into the prediction model, either sequentially (in techniques such as neural networks) or as a whole (in techniques that apply some form of regression, such as linear models, linear discriminant analysis, support vector machines). In some instances (e.g. k-nearest neighbours) the dataset (or subset of the dataset obtained after feature selection) is itself the model. As discussed, effective models can be established with minimal understanding of the detailed mathematics, through the use of various software packages where the parameters of the model have been pre-determined by expert analysts as most likely to lead to successful results.

Validation. This is a key component of the data-mining protocol, and the incorrect application of this frequently leads to errors. Portions of the dataset are to be set aside, apart from feature selection and training, to test the success of the prediction model. Furthermore, if the results of validation are used to effect feature selection and training of the model, then one obtains a further validation set to test the model before it is applied to real-life situations. If this process is not strictly adhered to the model is likely to fail in real-world situations. The methods of validation are described in more detail below.

Application. Once the model has been constructed, and validated, it must be packaged in some way as it is accessible to end users. This often involves implementation of some form a spreadsheet application, into which the model has been imbedded, scripting of a statistical software package, or refactoring of the model into a hard-coded application by information technology staff.

Examples of software packages that are frequently used are:

Spreadsheet plugins, obtained from multiple vendors.

The R statistical environment.

The commercial packages MatLab, S-plus. SAS, SPSS, STATA.

Free open-source software such as Octave (a MatLab clone)

many and varied C++ libraries, which can be used to implement prediction models in a commercial, closed-source setting.

Examples of Data Mining Methods

The methods of the invention can be performed by first undertaking the step of data mining (above), and then applying the appropriate known software packages. Further description of the process of data mining is described in detail in many extremely well-written texts[19].

Linear models[19,21]: The data is treated as the input of a linear regression model, of which the class labels or responses variables are the output. Class labels, or other categorical data, must be transformed into numerical values (usually integer). In generalised linear models, the class labels or response variables are not themselves linearly related to the input data, but are transformed through the use of a "link function". Logistic regression is the most common form of generalized linear model.

Linear Discriminant analysis[19,22,23]. Provided the data is linearly separable (i.e. the groups or classes of data can be separated by a hyperplane, which is an n-dimensional extension of a threshold), this technique can be applied. A combination of variables is used to separate the classes, such that the between group variance is maximised, and the within-group variance is minimised. The byproduct of this is the formation of a classification rule. Application of this rule to samples of unknown class allows predictions or classification of class membership to be made for that sample. There are variations of linear discriminant analysis such as nearest shrunken centroids which are commonly used for microarray analysis.

Support vector machines[24]: A collection of variables is used in conjunction with a collection of weights to determine a model that maximizes the separation between classes in terms of those weighted variables. Application of this model to a sample then produces a classification or prediction of class membership for that sample.

Neural networks[23]: The data is treated as input into a network of nodes, which superficially resemble biological neurons, which apply the input from all the nodes to which they are connected, and transform the input into an output. Commonly, neural networks use the "multiply and sum" algorithm, to transform the inputs from multiple connected input nodes into a single output. A node may not necessarily produce an output unless the inputs to that node exceed a certain threshold. Each node has as its input the output from several other nodes, with the final output node usually being linked to a categorical variable. The number of nodes, and the topology of the nodes can be varied in almost infinite ways, providing for the ability to classify extremely noisy data that may not be possible to categorize in other ways. The most common implementation of neural networks is the multi-layer perceptron.

Classification and regression trees[25]: In these, variables are used to define a hierarchy of rules that can be followed in a stepwise manner to determine the class of a sample. The typical process creates a set of rules which lead to a specific class output, or a specific statement of the inability to discriminate. A example classification tree is an implementation of an algorithm such as:

```
if gene A> x and gene Y > x and gene Z = z
then
    class A
else if geneA = q
    then
    class B
```

Nearest neighbour methods[22,23]. Predictions or classifications are made by comparing a sample (of unknown class) to those around it (of known class), with closeness defined by a distance function. It is possible to define many different distance functions. Commonly used distance functions are the Euclidean distance (an extension of the Pythagorean distance, as in triangulation, to n-dimensions), various forms of correlation (including Pearson Correlation co-efficient). There are also transformation functions that convert data points that would not normally be interconnected by a meaningful distance metric into euclidean space, so that Euclidean distance can then be applied (e.g. Mahalanobis distance). Although the distance metric can be quite complex, the basic premise of k-nearest neighbours is quite simple, essentially being a restatement of "find the k-data vectors that are most similar to the unknown input, find out which class they correspond to, and vote as to which class the unknown input is".

Other methods:
Bayesian networks. A directed acyclic graph is used to represent a collection of variables in conjunction with their joint probability distribution, which is then used to determine the probability of class membership for a sample.

Independent components analysis, in which independent signals (e.g., class membership) re isolated (into components) from a collection of variables. These components can then be used to produce a classification or prediction of class membership for a sample.

Ensemble learning methods in which a collection of prediction methods are combined to produce a joint classification or prediction of class membership for a sample There are many variations of these methodologies that can be explored[19], and many new methodologies are constantly being defined and developed. It will be appreciated that any one of these methodologies can be applied in order to obtain an acceptable result. Particular care must be taken to avoid overfitting, by ensuring that all results are tested via a comprehensive validation scheme.

Validation

Application of any of the prediction methods described involves both training and cross-validation[12,26] before the method can be applied to new datasets (such as data from a clinical trial). Training involves taking a subset of the dataset of interest (in this case gene expression measurements from melanoma), such that it is stratified across the classes that are being tested for (in this case tumours with good or poor likelihood of rapid progression). This training set is used to generate a prediction model (defined above), which is tested on the remainder of the data (the testing set).

It is possible to alter the parameters of the prediction model so as to obtain better performance in the testing set, however, this can lead to the situation known as overfitting, where the prediction model works on the training dataset but not on any external dataset. In order to circumvent this, the process of validation is followed. There are two major types of validation typically applied, the first (hold-out validation) involves partitioning the dataset into three groups: testing, training, and validation. The validation set has no input into the training process whatsoever, so that any adjustment of parameters or other refinements must take place during application to the testing set (but not the validation set). The second major type is cross-validation, which can be applied in several different ways, described below.

There are two main sub-types of cross-validation: K-fold cross-validation, and leave-one-out cross-validation.

K-fold cross-validation: The dataset is divided into K subsamples, each subsample containing approximately the same proportions of the class groups as the original.

In each round of validation, one of the K subsamples is set aside, and training is accomplished using the remainder of the dataset. The effectiveness of the training for that round is gauged by how correctly the classification of the left-out group is. This procedure is repeated K-times, and the overall effectiveness ascertained by comparison of the predicted class with the known class.

Leave-one-out cross-validation: A commonly used variation of K-fold cross validation, in which K=n, where n is the number of samples.

Combinations of MPMS, such as those described above in Table 1, can be used to construct predictive models for prognosis.

Prognostic Signatures

Prognostic signatures, comprising one or more of these markers, can be used to determine the outcome of a patient, through application of one or more predictive models derived from the signature. In particular, a clinician or researcher can determine the differential expression (e.g., increased or decreased expression) of the one or more markers in the signature, apply a predictive model, and thereby predict the negative prognosis, e.g., likelihood of disease relapse, of a patient, or alternatively the likelihood of a positive prognosis (continued remission).

A prognostic signature has been developed. As described in the Example below, a prognostic signature comprising 22 genes has been established from a set of patients with melanoma (Table 1). By obtaining a patient sample (e.g., tumour sample), and matching the expression levels of one or more markers in the sample to the differential expression profile, the likelihood of the cancer progressing rapidly can be determined.

Drug Trials

The present invention can also be used to select individuals for particular drug trials. By establishing the prognosis of an individual with melanoma, then a better decision can be made on whether a patient should undergo conventional treatment for which they are likely to respond to, or whether they should participate in a particular drug trial that is aim at a particular tumour type or stage.

The selection of patients with a short predicted time to disease progression would also enable the shortening of the duration of drug trials and allow fewer patients to be enrolled to achieve statistically significant drug response data.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

To investigate biological mechanisms within tumors which may affect clinical outcome in stage III melanoma, gene expression profiling was performed on an initial test set of 29 melanoma specimens from patients with diverse clinical outcome following lymphadenectomy for Stage IIIB and IIIC melanoma. This was then used to prospectively predict clinical outcome based on a molecular profile in two independent validation sets comprising 10 and 14 patients. Using this molecular information, cellular pathways and networks were also identified which may be differentially regulated between the two patient groups and are possible targets for therapeutic intervention.

Materials and Methods

Specimen Collection and Selection for Microarray Analysis

Figure 3:
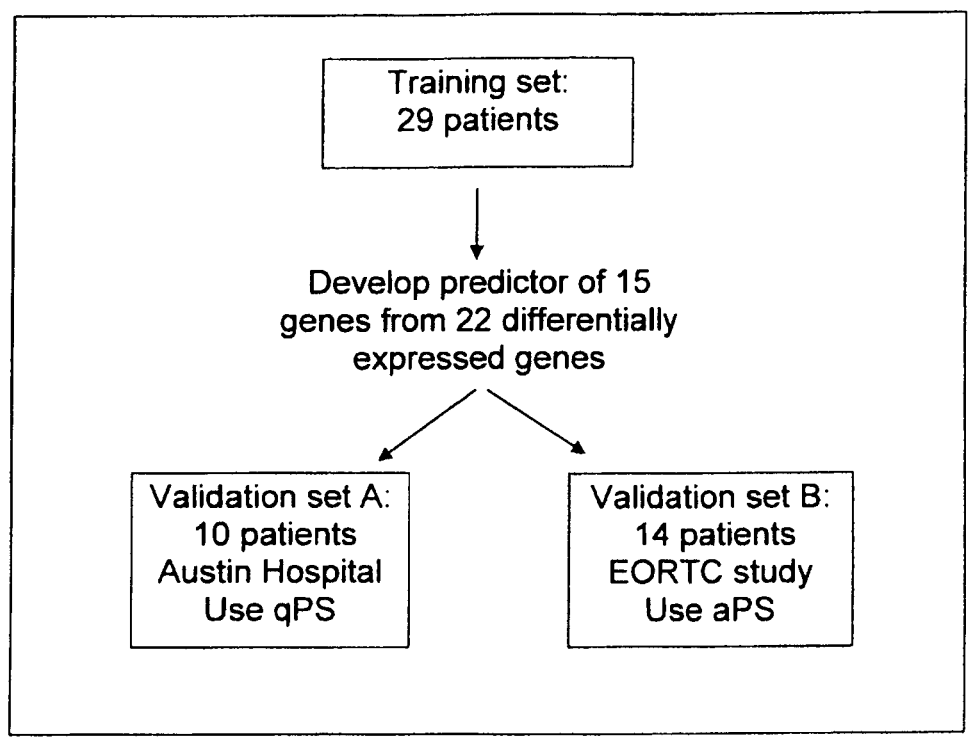
FIG. 3 Experimental schema comprising a training set and two independent applied to Validation Set A using the qPS and Set B using the aPS. The training set was used to develop predictive genes which were then applied to Validation Set A using the qPS and Set B using the aPS.

The overall schema of the experiments performed is represented in FIG. 3. Ex vivo melanoma tissue from 29 patients who underwent surgical lymphadenectomy for clinically palpable nodes between 1997 and 2004 at Austin Health were selected for microarray analysis. All specimens were collected under a tissue procurement protocol approved by the Austin Health Human Research Ethics Committee and with the written informed consent of each patient. Snap frozen specimens were embedded in optimal cutting temperature compound (OCT) and stored as tissue blocks at −80° C. within the Ludwig/Austin tissue bank repository. Diagnosis was confirmed by a pathologist in all cases.

Patient samples were selected for microarray analysis on the basis of time taken to tumor progression (TTP) from Stage III to Stage IV disease and included 16 "poor" (mean TTP 4 months) and 13 "good" (mean TTP 42 months) prognosis patients. Post operative reviews in a dedicated Melanoma Unit were carried out on a monthly basis for the initial 12 months post-lymphadenectomy, followed by three and six monthly reviews thereafter according to clinical requirement until four years, with annual review thereafter. Staging investigations were performed according to clinical suspicion or routinely every 3-6 months.

Tissues were considered acceptable for this study if minimal necrosis was present and tumor cells comprised at least 60% of the total cell population. At the time of RNA extraction, two 5 µm sections were cut and stained with hematoxylin and eosin to ensure integrity of the extracted tissue.

RNA Extraction and cDNA Synthesis cDNA synthesis and hybridization with a common reference design were conducted in duplicate for the 29 selected patients. Total RNA was extracted from OCT embedded tissue by immersing and homogenizing tissue sections in Tri-reagent (Molecular Research Center, Cincinnati, Ohio.) 1.5 mL of chloroform was added to the homogenate, the sample centrifuged, and the top phase was removed and mixed with 100% ethanol. Purification using an RNeasy column was performed according to the manufacturer's instructions (Qiagen, Valencia, Calif.). RNA quality was confirmed on the basis of 260:280 ratios of absorbances and integrity was inspected on formaldehyde-agarose gels against rRNA standard markers. cDNA was synthesized from 20 µg of RNA in the presence of oligo(dT) and amino allyl deoxynucleotide. Cy dyes (Amersham Biosciences, Buckinghamshire, UK) were coupled to tumor cDNA and reference cDNA produced in parallel. Reference cDNA was synthesized from pooled RNA from a variety of tumors and cell lines including melanoma, as well as from normal tissues (see FIG. 4).

Oligonucleotide Arrays and Data Analysis 30,888 oligonucleotide probes, representing individual genes and internal controls, were obtained from MWG Biotech (Erbesberg, Germany) and spotted as high density arrays using an Omnigrid robot (Gene Machines, San Carlos, Calif.). Labeled tumor/reference cDNA was co-hybridized and scanned using a Genepix 4000A microarray scanner (Axon Instruments, Union City, Calif.). The matrix overlay was aligned to the scanned image and feature extraction performed using Gene Pix v6.0 software (Axon Instruments, Foster City, Calif.). The raw data was analyzed using Gene-Spring v7.2 (Silicon Genetics, Redwood City, Calif.). The data was normalized to print-tip group and then median normalized. Briefly, a lowess curve was fit to the log-intensity versus log-ratio plot. Twenty percent of the data was used to calculate the lowess fit at each point. This curve was used to adjust the control value for each measurement. Each gene was then divided by the median of its measurements in all samples.

Data for independent validation set B from the EORTC melanoma study[27], was made available through the Array Express public data repository: http://www.ebi.ac.uk/arrayexpress/. The data was uploaded into Genespring v7.2 and normalized per spot, per chip and per gene. In brief each gene's measured intensity was divided by its control channel value in each sample and then divided by the 50th percentile of all measurements in that sample. Finally each gene was divided by the median of its measurements in all samples. Expression values for the differentially expressed genes were used to calculate a predictive score as described below.

Statistical Methods

Gene expression data was first subjected to a filter that excluded probes which were not present in all samples. Of the initial 30,888 probes considered, 18,807 passed this filter and were used for analysis of variance, hierarchical clustering and principal component analysis. Differentially expressed genes were discovered by performing a Wilcoxon-Mann-Whitney test with the false discovery rate controlling method of Benjamini and Hochberg[28] used to correct for multiple testing correction based on a p-value cut-off of 0.05. Hierarchical clustering of samples was performed using Spearman correlation as the distance function and average linkage.

Quantitative Real Time PCR (qPCR)

qPCR was performed on differentially expressed genes to confirm the array results, and then in validating the predictor using validation set A. First strand cDNA was synthesized from 2 µg of total RNA extracted for the array experiment using a random hexamer primer (Promega, Madison, Wis.). Negative controls were obtained by omitting reverse transcriptase. Intron-spanning multiplex assays were designed for qPCR (see FIG. 5 for assay design) using the Universal Probe Library assay design centre https://www.roche-applied-science.com/ (Roche, Mannheim, Germany). All reactions were carried out in duplicate using the ABI 7700 sequence detector (Applied Biosystems, Foster City, Calif.). Thermal cycler conditions were as follows: 50° C. for 2 minutes, 95° C. for 10 minutes followed by 40 cycles of 94° C. for 20 seconds and 60° C. for 45 seconds. All results were normalized to 18 S amplification (Applied Biosystems, Foster City, Calif.). We calculated relative expression using the target threshold ($C_T$) value for reference as our comparator[29].

The relative expression values for individual genes were then plotted along side the normalized $\log_2$ ratio array values and correlation coefficients calculated.

Results

Clinical and pathological features for the patients included in the test set and validation set A are listed (see FIG. 6). All patients had information on age at initial diagnosis, sex, and number and location of positive lymph nodal metastases. Not all patients had their initial diagnosis made at our hospital and so in some cases we were unable to ascertain whether ulceration was present in the primary melanoma. Ulceration in the primary is an independent prognostic factor which if present upstages the disease from IIIB to IIIC[30].

The mean TTP for the "good" prognosis group was 40 months compared to 4 months in the "poor" group. There were no statistically significant differences in the median age and sex between the groups, although the "good" group appeared younger and contained more women. There were no statistically significant differences in other known prognostic characteristics including AJCC staging, the use of adjuvant interferon and the presence of tumor infiltrating lymphocytes, although there was a limitation of the sample size.

One patient had isolated Stage IV disease confined to resected spleen, but given that they remained disease-free this sample was included. Exclusion of this sample did not alter the gene expression profile.

Differentially Expressed Genes Segregate the Two Prognostic Groups

Unsupervised hierarchical clustering did not reveal subgroups of melanomas which correlated with prognostic nor other clinical information, which was expected given the similarities between the samples. To search for genes which could effectively segregate the prognostic groups, differential gene expression was investigated. 2,140 genes were differentially expressed between the two groups, however the stringent application of multiple testing correction reduced this to 22 genes with highly significant differential expression (FIG. 1). The 22 genes were further validated in the training set using qPCR and the genes with the highest correlation co-efficient between the two platforms (r>0.5, p<0.05) were selected for further analysis (data not shown). Of the initial 22, fifteen genes exhibited high cross-platform correlation and these were used in the development of a predictive score. Principal Components Analysis demonstrated the ability of the 15 genes to segregate the prognostic groups (FIG. 7).

Development of Predictive Scores

The initial test set was used to develop a predictor which was tested on two independent validation sets. Two predictive algorithms were developed based on the array data and then the qPCR data:

1. To calculate a predictive score for the array data (aPS), the fifteen genes with the most significant correlation between the array and qPCR were used. The normalized $\log_2$ expression ratios were transformed by raising the values to the power of two. Genes down regulated in the "good" prognostic group were ascribed a negative value. The final score was then calculated by the sum of values for all fifteen genes. A positive score was associated with improved outcome.

2. For the qPCR data (qPS), $\Delta\Delta C_T$ values for the fifteen most correlated genes were applied to a logistic regression algorithm which utilizes Akaike Information Criterion to select only those genes which contribute to class distinction. This selected five significant genes which were then used in the following equation:

$$qPS=[1328.15-187.42(IDH)+137.10(MFG8)+73.61(PILRA)+211.22(HLA\text{-}E)+143.94(TXNDC5)]\times-1$$

As with the aPS, a positive score was associated with improved outcome using this method.

The Predictive Scores Correlate with TTP and Survival

Figure 8:
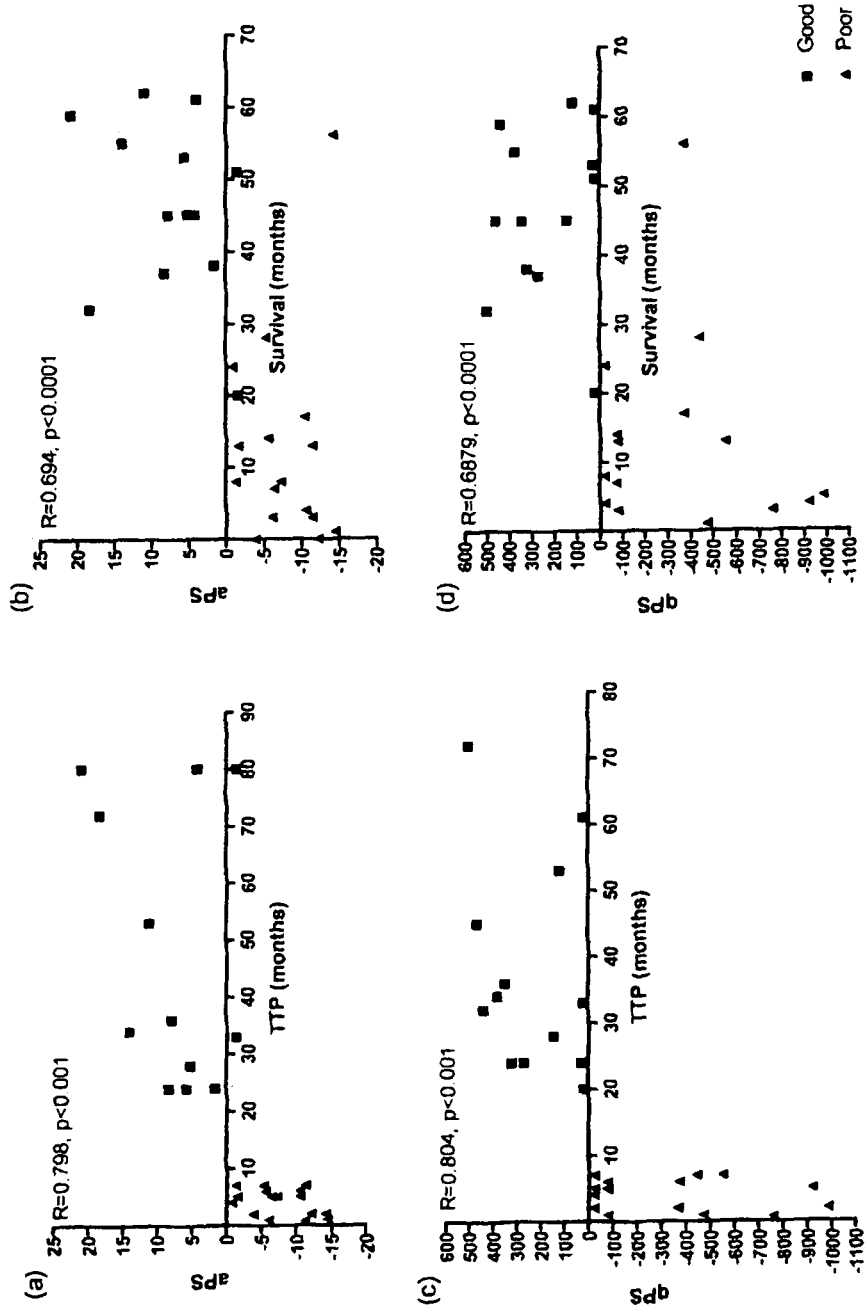
FIG. 8 depicts the application of the aPS (a-b) and qPS (c-d) in the training set demonstrating its correlation with TTP and overall survival. The aPS used only the 15 genes with the strongest correlation between the array data and qPCR data and the qPS used the five genes with the greatest ability to separate the two groups.

As expected, both the aPS and qPS applied to the test set were capable of distinguishing the two prognostic groups. A strong correlation between individual scores and both TTP and overall survival were evident, such that the magnitude of individual scores (high scores with aPS and negative scores for qPS) correlated with improved outcome for both the qPS and aPS (FIG. 8, Spearman rank correlation r=0.7908, p<0.0001). This suggests that the expression level of these differentially expressed genes is related to underlying biological mechanisms which directly influence clinical outcome, emphasizing their prognostic relevance.

Application of the Predictive Score to Three Independent Sets

The results were then applied on independently generated data. One published dataset with a subgroup of similar patients to our own was identified. Of the 83 patients who were profiled in this study[27], 14 had Stage III disease with long term follow, up. In this subgroup, ten patients would have been classified as "poor" (mean TTP 10 months) and four "good" (mean TTP 62 months) using similar criteria applied in our test set. When the aPS algorithm was applied to these samples, all ten "poor" patients and two of the four "good" patients were correctly predicted, yielding an overall correct classification rate of 85%.

Figure 9:
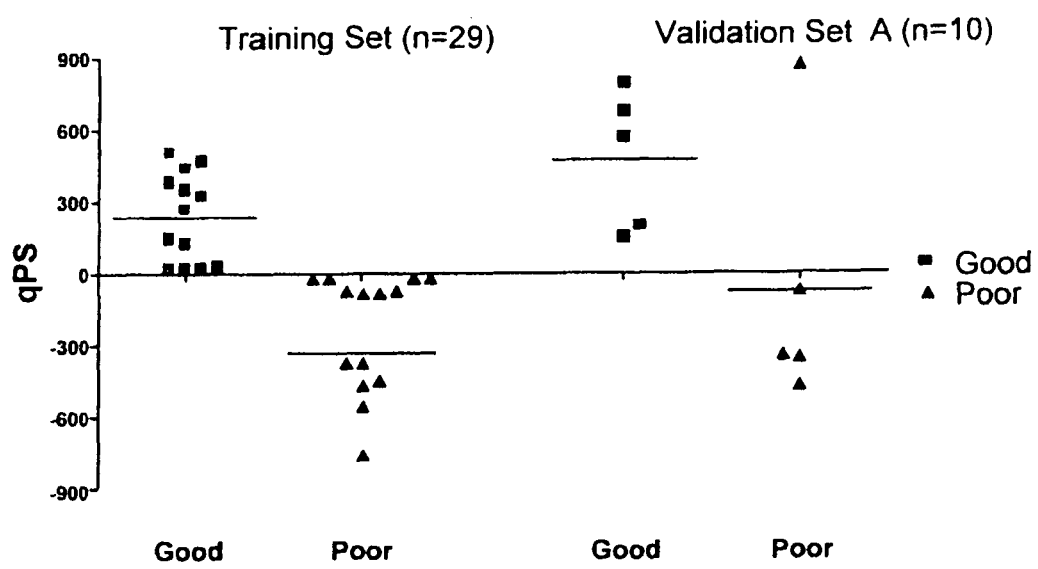
FIG. 9 depicts the qPS logistic regression algorithm applied to the training set and validation set A. A horizontal line is drawn at mean values.

Next we applied the qPS algorithm to an independent set of ten tumors from the Ludwig/Austin tissue bank for which qPCR assays were conducted using the five most powerfully predictive genes. The predictor correctly classified all five of the "good" prognosis tumors but misclassified of the five "poor" samples (FIG. 9). The incorrectly classified "poor" sample represented a patient in whom TTP was brief, but who had a prolonged overall survival of six years with metastatic disease.

Figure 10:
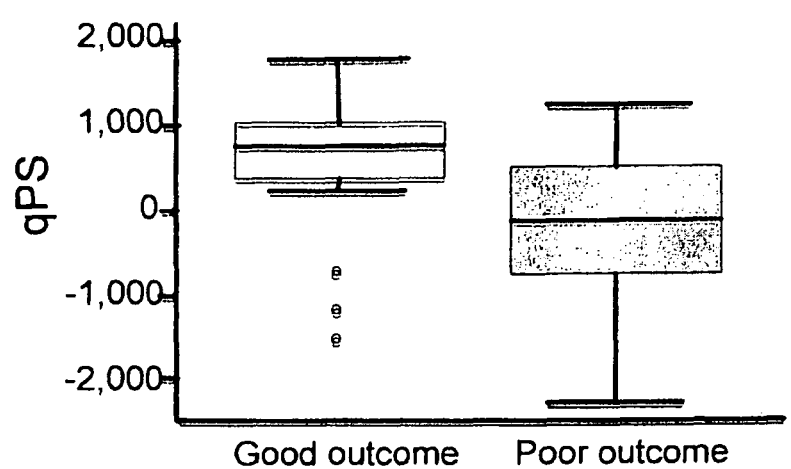
FIG. 10 depicts the distribution of the qPS scores from the good and poor prognostic groups of third independent set.

The five gene qPS was also applied to a third, independent set of stage 3 melanoma samples. These samples were composed of 19 patients with survival of under 18 months following diagnosis of stage 3 disease and a further 18 patients who survived greater than four years from stage 3 diagnosis. The distributions of the qPS scores from these good and poor prognostic groups were significantly different (p=0.02) and are shown in FIG. 10.

Discussion

This example shows the successful prediction of clinical outcome in an otherwise indistinguishable group of Stage III melanoma patients using an expression profile derived from microarray gene expression data and qPCR. In two independent sets it has been established that the two developed predictive score algorithms, which is based on 15 differentially expressed genes, can be applied to microarray and qPCR data to prospectively predict clinical outcome in patients with Stage IIIB/C melanoma.

These patients were selected for similar stage disease and several studies have demonstrated more similarities in gene expression amongst autologous samples taken at different stages than between patients with similar stage disease[27,31,32]. The observation that there are genes differentially expressed between the groups which can be used to prospectively predict outcome with up to 92% accuracy, underscores their importance. Furthermore the correlation of the predictor with both TTP and overall survival also highlight the utility of the predictor such that the magnitude of difference in scores directly correlates with clinical outcome.

Wherein in the description reference has been made to integers or components having known equivalents, such equivalents are herein incorporated as if individually set fourth. Although the invention has been described by way of example and with reference to possible embodiments thereof, it is to be appreciated that improvements and/or modifications may be made without departing from the scope thereof.

REFERENCES

1. Australian Institute of Health and Welfare (AIHW): Cancer in Australia 2001. Canberra. Australian Institute of Health and Welfare
Australsian Association of Cancer Registries (AACR), 2004
2. Florez A, Cruces M: Melanoma epidemic: true or false? Int J Dermatol 43:405-7, 2004
3. Thursfield V, Farrugia H, Giles G: Cancer in Victoria 2004, Canstat. Victoria, Cancer Epidemiology Centre, 2006, pp 32
4. Thompson J F, Scolyer R A, Kefford R F: Cutaneous melanoma. Lancet 365:687-701, 2005
5. Verma S, Quirt I, McCready D, et al: Systematic review of systemic adjuvant therapy for patients at high risk for recurrent melanoma. Cancer 106:1431-42, 2006
6. Hersey P: Adjuvant therapy for high-risk primary and resected metastatic melanoma. Intern Med J 33:33-43, 2003
7. Kirkwood J M, Manola J, Ibrahim J, et al: A pooled analysis of eastern cooperative oncology group and intergroup trials of adjuvant high-dose interferon for melanoma. Clin Cancer Res 10:1670-7, 2004
8. Sondak V K, Sabel M S, Mule J J: Allogeneic and autologous melanoma vaccines: where have we been and where are we going? Clin Cancer Res 12:2337s-2341s, 2006
9. Balch C M, Sober A J, Soong S J, et al: The new melanoma staging system. Semin Cutan Med Surg 22:42-54, 2003
10. Kirkwood J M, Strawderman M H, Ernstoff M S, et al: Interferon alfa-2b adjuvant therapy of high-risk resected cutaneous melanoma: the Eastern Cooperative Oncology Group Trial EST 1684. J Clin Oncol 14:7-17, 1996
11. Kirkwood J M, Ibrahim J G, Sondak V K, et al: High- and low-dose interferon alfa-2b in high-risk melanoma: first analysis of intergroup trial E1690/S9111/C9190. J Clin Oncol 18:2444-58, 2000
12. Efron, B. and Tibshirani, R. An Introduction to the Bootstrap. Chapman & Hall. 2005
13. McLaughlan G J, Do K, Ambroise C Analyzing Microarray Gene Expression Data (Wiley Series in Probability and Statistics) 2004
14. Wright G W, Simon R M A random variance model for detection of differential gene expression in small microarray experiments. Bioinformatics 2003; 19:2448-2455.
15. Smyth G K. Linear models and empirical Bayes methods for assessing differential expression in microarray experiments. Statistical Applications in Genetics and Molecular Biology 2004; 3:Article 3.
16. Lönnstedt I. and Speed T P. Replicated microarray data. Statistica Sinica 2002; 12:31-46.
17. Ihaka R, Gentleman R. R: A language for data analysis and graphics. Journal of Computational and Graphical Statistics 1996;5:299-314.
18. Becker R A, Chambers, J M and Wilks A R The New S Language. Wadsworth & Brooks/Cole 1988.
19. Hastie T, Tibshirani R, Friedman J The Elements of Statistical Learning Data Mining, Inference and Prediction Springer 2003
20. Gentleman R., Carey V J, Huber W., Irizarry, R A, Dudoit S. Bioinformatics and Computational Biology Solutions Using R and Bioconductor. Springer 2005.
21. Neter J, Kutner M H, Wasserman W, Nachtsheim C J. Applied Linear Statistical Models McGraw-Hill/Irwin 1996
22. Venables, W N, Ripley, B D Modern Applied Statistics with S. $4^{th}$ ed. Springer 2002.
23. Ripley, B. D. Pattern Recognition and Neural Networks Cambridge University Press 1996
24. Cristianini N, Shawe-Taylor J An Introduction to Support Vector Machines (and other kernel-based learning methods) Cambridge University Press 2000
25. Breiman L, Friedman J, Stone C J, Olshen R A Classification and Regression Trees Chapman & Hall/CRC 1984
26. Good, P I Resampling Methods: A Practical Guide to Data Analysis Birkhauser 1999
27. Winnepenninckx V, Lazar V, Michiels S, et al: Gene expression profiling of primary cutaneous melanoma and clinical outcome. J Natl Cancer Inst 98:472-82, 2006
28. Benjamini Y, Hochberg Y: Controlling the false discovery rate: a practical and powerful approach to multiple testing. Journal of the Royal Statistical Society 57:289-300, 1995
29. Livak K J, Schmittgen T D: Analysis of relative gene expression data using real-time quantitative PCR and the 2(-Delta Delta C(T)) Method. Methods 25:402-8, 2001
30. Balch C M, Sober A J, Soong S J, et al: The new melanoma staging system. Semin Cutan Med Surg 22:42-54, 2003
31. Wang E, Miller L D, Ohnmacht G A, et al: Prospective molecular profiling of melanoma metastases suggests classifiers of immune responsiveness. Cancer Res 62:3581-6, 2002
32. Ramaswamy S, Ross K N, Lander E S, et al: A molecular signature of metastasis in primary solid tumors. Nat Genet 33:49-54, 2003

INDUSTRIAL APPLICABILITY

The methods, compositions, kits, and devices of the invention, which are based on prognostic cancer markers, specifically melanoma prognostic markers, are useful for the prognosis and treatment of cancer, particularly melanoma.

The invention claimed is:

1. A method for predicting the prognosis of a melanoma in a patient with stage IIIB or stage IIIC cutaneous melanoma after lymphadenectomy, comprising measuring in a melanoma tumor sample from the patient, expression of the genes milk fat globule EGF factor 8 protein (MFGE8), isocitrate dehydrogenase 1 (NADPH+ soluble (IDH1), paired immunoglobin-like type 2 receptor alpha (PILRA), major histocompatibility complex class 1E (HLA-E) and thioredoxin domain containing 5 (TXNDC5), and wherein expression of each of said genes from a sample from a patient is determined using qPCR to quantify mRNA expression; and calculating a score ("qPS") according to the formula:

$$qPS=-[1328.15-187.42(IDH1)+137.10(MFGE8)+73.61(PILRA)+211.22(HLA-E)+143.94(TXNDC5)],$$

where in said formula, IDH1 means $\Delta\Delta C_t$ for isocitrate dehydrogenase 1, MFGE8 means $\Delta\Delta C_t$ for milk fat globule EGF factor 8 protein, PILRA means $\Delta\Delta C_t$ for paired immunoglobin-like type 2 receptor alpha, HLA-E means $\Delta\Delta C_t$ for major histocompatibility complex, class 1E, and TXHDC5 means $\Delta\Delta C_t$ for thioredoxin domain containing 5, wherein a qPS score of less than zero indicates poor prognosis with respect to time to progression (TTP) and overall survival and a qPS score of greater than zero indicates good prognosis with respect to time to progression (TTP) and overall survival.

* * * * *

UNITED STATES PATENT AND TRADEMARK OFFICE
CERTIFICATE OF CORRECTION

PATENT NO.         : 8,822,149 B2
APPLICATION NO.    : 12/592385
DATED              : September 2, 2014
INVENTOR(S)        : Michael Alan Black et al.

It is certified that error appears in the above-identified patent and that said Letters Patent is hereby corrected as shown below:

In the Claims

Column 29, line 16: Delete "qPS=-/1328.15"

and add: –qPS=-[1328.15–

Signed and Sealed this
Twenty-first Day of October, 2014

Michelle K. Lee
*Deputy Director of the United States Patent and Trademark Office*